(12) United States Patent
Shin

(10) Patent No.: US 8,961,534 B2
(45) Date of Patent: Feb. 24, 2015

(54) MEDICAL SNARE

(75) Inventor: Kyong Min Shin, Seoul (KR)

(73) Assignees: Taewoong Medical Co., Ltd., Gyeonggi-do (KR); Kyong Min Shin, Seoul (KR)

( * ) Notice: Subject to any disclaimer, the term of this patent is extended or adjusted under 35 U.S.C. 154(b) by 0 days.

(21) Appl. No.: 13/977,494

(22) PCT Filed: Jan. 17, 2012

(86) PCT No.: PCT/KR2012/000371
§ 371 (c)(1),
(2), (4) Date: Jun. 28, 2013

(87) PCT Pub. No.: WO2012/102508
PCT Pub. Date: Aug. 2, 2012

(65) Prior Publication Data
US 2013/0296878 A1    Nov. 7, 2013

(30) Foreign Application Priority Data

Jan. 25, 2011 (KR) .................. 10-2011-0007380
Sep. 6, 2011 (KR) .................. 10-2011-0090231

(51) Int. Cl.
*A61B 17/3205* (2006.01)
*A61M 25/01* (2006.01)

(52) U.S. Cl.
CPC ...... *A61B 17/32056* (2013.01); *A61M 25/0102* (2013.01)
USPC ........................................ 606/113

(58) Field of Classification Search
CPC ............. A61B 17/26; A61B 17/32056; A61B 2017/2212; A61B 17/221
USPC ........... 606/41, 137, 128, 127, 112, 111, 113, 606/110, 167, 139, 108; 600/562, 564, 570, 600/571, 573; 623/1.1, 1.2, 1.23
See application file for complete search history.

(56) References Cited

U.S. PATENT DOCUMENTS

| | | | |
|---|---|---|---|
| 6,673,092 B1 * | 1/2004 | Bacher | 606/205 |
| 7,758,593 B2 * | 7/2010 | Nobis et al. | 606/113 |
| 2003/0109888 A1 * | 6/2003 | Mercereau et al. | 606/127 |
| 2003/0135222 A1 | 7/2003 | Baska | |
| 2005/0043743 A1 | 2/2005 | Dennis | |
| 2009/0112225 A1 * | 4/2009 | Kaneko et al. | 606/113 |

FOREIGN PATENT DOCUMENTS

| | | |
|---|---|---|
| WO | WO 95/31943 | 11/1995 |
| WO | WO 01/67967 | 9/2001 |

* cited by examiner

*Primary Examiner* — Jonathan W Miles
*Assistant Examiner* — George J Ulsh
(74) *Attorney, Agent, or Firm* — IP & T Group LLP

(57) ABSTRACT

Provided a medical snare in which the expansion direction of a loop is easily rotated in an arbitrary direction in which a removable target has grown, the removable target is easily inserted into the loop so as to allow a surgical procedure to be easily performed to reduce a time required for the surgical procedure and burdens of a patient and a surgeon, and the free rotation of a wheel is prevented to be able to fix the expansion direction of the loop. Accordingly, only the wheel can be easily rotated to switch the expansion direction of the loop without rotating the entire medical snare.

4 Claims, 8 Drawing Sheets

MEDICAL SNARE

This application is a national stage application of PCT/KR2012/000371 filed on Jan. 17, 2012, which claims priority of Korean patent application number 10-2011-0007380 and 10-2011-0090231 filed on Jan. 25, 2011 and Sep. 6, 2011, respectively. The disclosure of each of the foregoing applications is incorporated herein by reference in its entirety.

TECHNICAL FIELD

The present invention relates, in general, to a medical snare and, more particularly, to a medical snare in which the expansion direction of a loop is easily rotated in an arbitrary direction in which a removable target has grown, the removable target is easily inserted into the loop so as to allow a surgical procedure to be easily performed to reduce time required for the surgical procedure and burdens of a patient and a surgeon, and free rotation of a wheel is prevented to be able to fix the expansion direction of the loop.

BACKGROUND ART

Such a type of polypectomy snare has already been known in DE 7835595. The known polypectomy snare or diathermy snare is made up of a tensile wire. The tensile wire enters a loop similar to a semicircle at a front end thereof and comes to an end there. The loop has a peak. The tensile wire is easily guided in a bushing and a corresponding pipe-shaped stopper member disposed at an end of the bushing. One of two legs of the loop is fixedly connected to the tensile wire. As a result, the loop can be displaced from a storage position at which the loop is placed in the bushing in an expanded state to a use position at which the loop is located in front of an end of the bushing by the tensile wire. The other leg of the loop which is located in the bushing is connected to a stopper moving toward a corresponding stopper in the process of extracting the loop out of the bushing. As a result, when the other leg of the loop continues to move, the loop is expanded, in a semi-circular shape.

A high-frequency resection apparatus capable of supplying electric current to a snare as described above is known in DE 2951060. Here, the snare acts as an electrode. The apparatus formed in this way is used to resect abdominal tissue such as a tumor using high-frequency current according to a system for resecting a region that is located in an abdominal cavity, particularly in an intestine, and that has a tumor, for instance one or more polyps. In the region, the high-frequency current can flow between an electrode, which is intended for resection and is formed by a snare-shaped conductive wire guided into the cavity, and an outer electrode, which is fixed to skin of a patient and is disposed apart from the resection electrode.

In the event of resection, a surgeon should, typically place a loop inserted into the abdominal cavity on the polyp using an endoscope.

This conventional polypectomy snare is rotated as a whole in order to insert the loop to a spot where the polyp to be removed has grown along with an endoscope and rotate the direction of the loop in the direction in which the polyp has grown, thereby facilitating the insertion of the polyp into the loop. Since the entire polypectomy snare is rotated, there is a problem in that the surgeon cannot smoothly rotate the loop in a desired direction and a burden imposed on a wrist is increased.

For this reason, a medical snare for removing the polyp, which can easily rotate an expansion direction of the loop in the direction in which the polyp has grown and that allows the polyp to be smoothly inserted into the loop to reduce time required for the surgical procedure and to easily perform the surgical procedure, is urgently required.

DISCLOSURE

Technical Problem

Accordingly, the present invention has been made keeping in mind the above problems occurring in the related art, and is intended to provide a medical snare that allows an expansion direction of a loop to be easily rotated by rotation of a wire alone without rotating the entire medical snare.

Further, the present invention serves to provide a medical snare in which a wheel is coupled to an auxiliary pusher to which a wire is connected and is rotated, thereby allowing the auxiliary pusher and the wire to be rotated to easily switch a direction of a loop so that a removable target is smoothly inserted.

Further, the present invention serves to provide a medical snare in which engaging faces of an auxiliary pusher are engaged with an engaged hole of a wheel, thereby allowing the wheel to be accurately rotated without sliding when the wheel is rotated.

In addition, the present invention serves to provide a medical snare in which locking protrusions are inserted into locked recesses of a wheel thereby preventing the wheel from being restored to its original position by a rotational restoring force of a wire after an expansion direction of a loop is rotated by rotation of the wheel, and preventing the expansion direction of the loop from being changed.

Technical Solution

In an aspect, the present invention provides a medical, snare in which: a pusher is coupled in front of a movable handle moving along a cylindrical body in a forward/backward direction; a wire, at a front end of which a loop is formed, is connected to a front end of the pusher along an interior of a tube coupled to the front of the cylindrical body; tissue is inserted into the loop exposed from the tube by forward movement of the movable handle and is cut by backward movement of the movable handle so as to perform a surgical procedure; an auxiliary pusher having engaging faces on an outer circumference is rotatably coupled to the front end of the pusher of the movable handle; the wire having the loop is fixedly coupled to a front end of the auxiliary pusher; a wheel, in the center of which an engaged hole is formed so as to be fitted around the auxiliary pusher, is installed at a front side of the body so as to not be separated; when the movable handle moves forward/backward, the auxiliary pusher slidably passes through the engaged hole of the wheel; and when the wheel is rotated, the auxiliary pusher and the wire are rotated so as to be able to switch an open direction of the loop due to the engagement of the engaging faces and the engaged hole.

Advantageous Effects

According to the medical snare as described above, an expansion direction of a loop can be easily rotated by rotation of a wire alone without rotating the entire medical snare.

Further, a wheel is coupled to an auxiliary pusher to which a wire is connected, and is rotated. Thereby, the auxiliary pusher and the wire can be rotated to easily switch a direction of a loop so that a removable target is smoothly inserted.

Further, engaging faces of an auxiliary pusher are engaged with an engaged hole of a wheel, such that the wheel can foe accurately rotated without sliding when the wheel is rotated.

In addition, locking protrusions are inserted into locked recesses of a wheel. Thereby, the wheel is prevented from being restored to its original position by a rotational restoring force of a wire after an expansion direction of a loop is rotated by rotation of the wheel, and the expansion direction of the loop is prevented from being changed.

LISTS OF SYMBOLS USED FOR MAIN PARTS OF THE DRAWINGS

Figure 1:
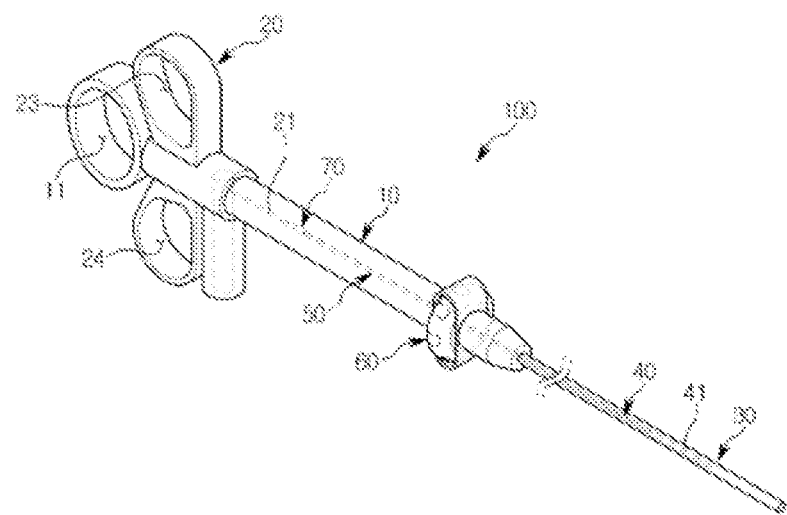
FIG. 1 is a perspective view of a medical snare according to the present invention.
Figure 2:
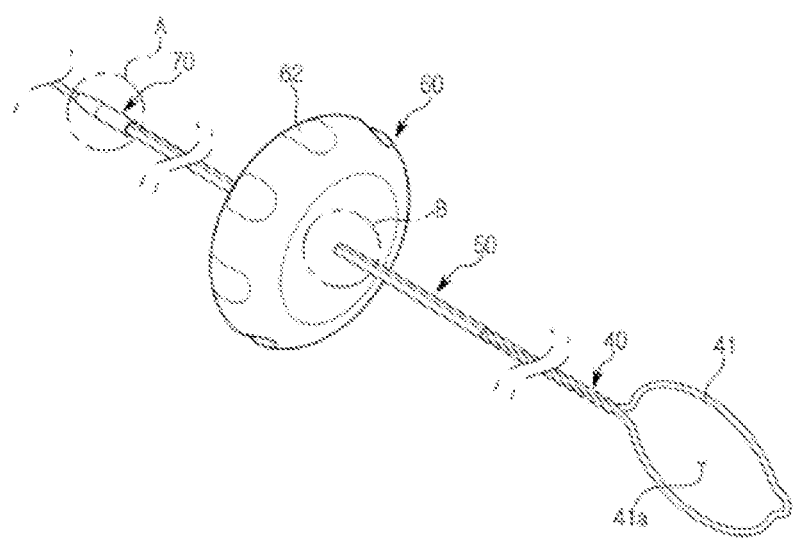
FIG. 2 is a partial extraction view of the medical snare according to the present invention wherein a wheel and an auxiliary pusher are connected.
Figure 3:
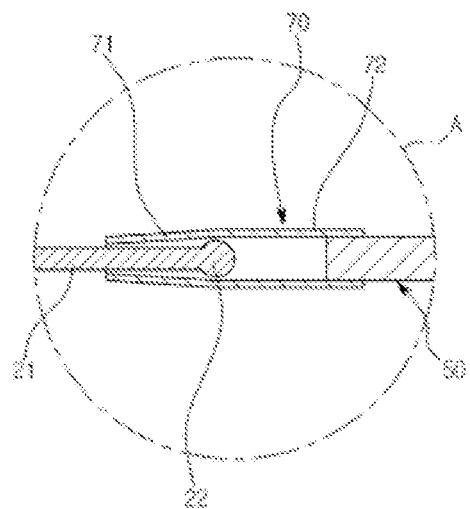
FIG. 3 is a cross-sectional view showing a state in which the auxiliary pusher is connected to a connecting pipe in part A of FIG. 2.
Figure 4:
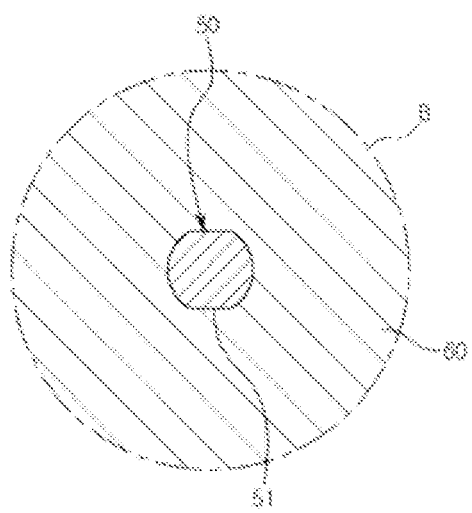
FIG. 4 is a cross-sectional view showing a state in which a wheel and the auxiliary pusher according to the present invention are connected in part B of FIG. 2.
Figure 5:
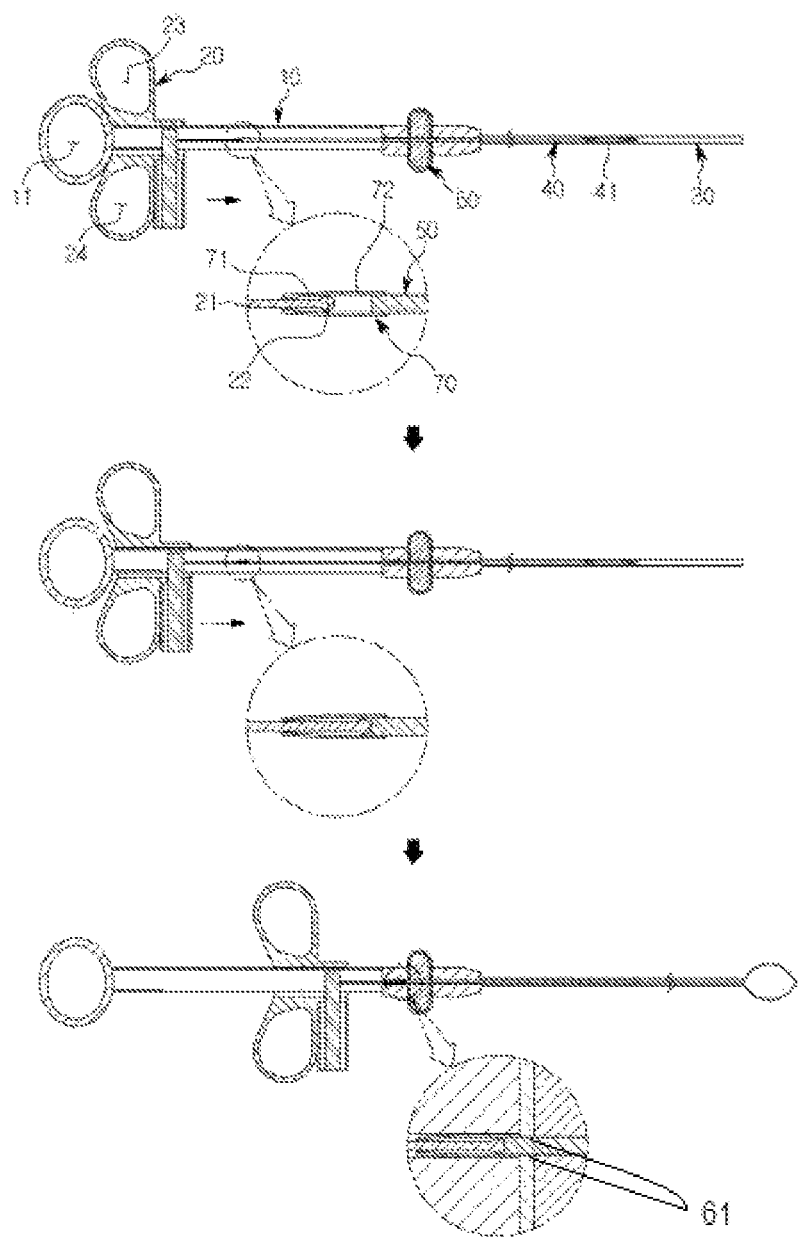
FIG. 5 is a view showing drawing and inserting operations of a wire based on an operation of a movable handle of the medical snare according to the present invention.
Figure 6:
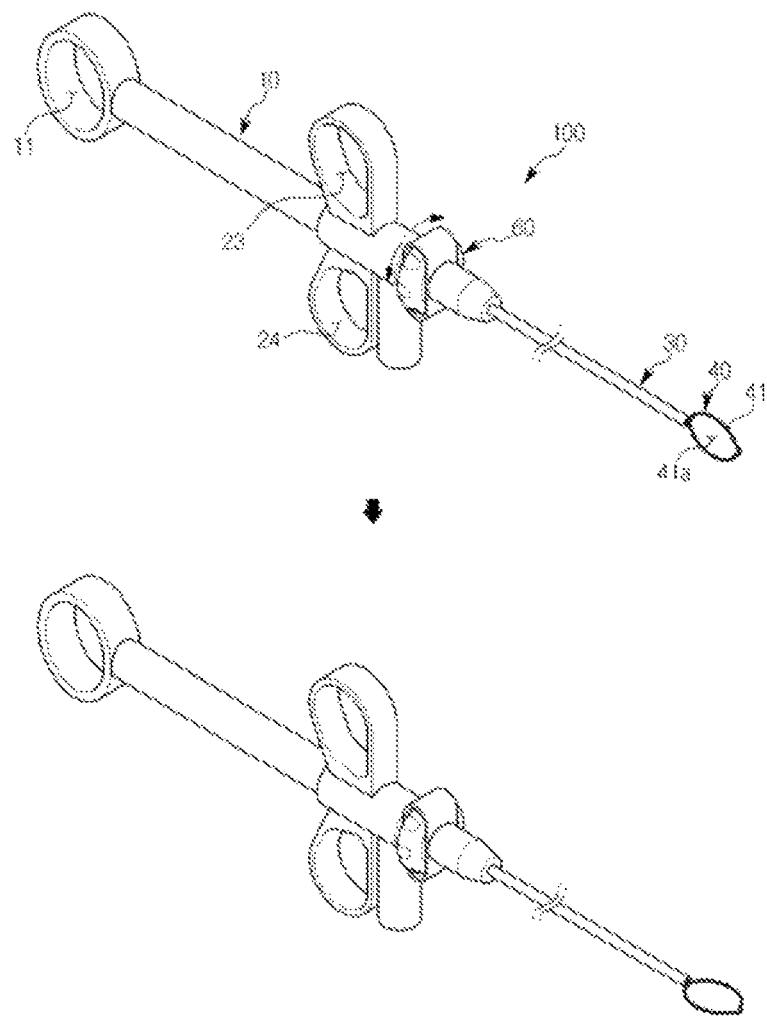
FIG. 6 is a perspective view showing rotation of the wire when the wheel of the medical snare according to the present invention is rotated.
Figure 7:
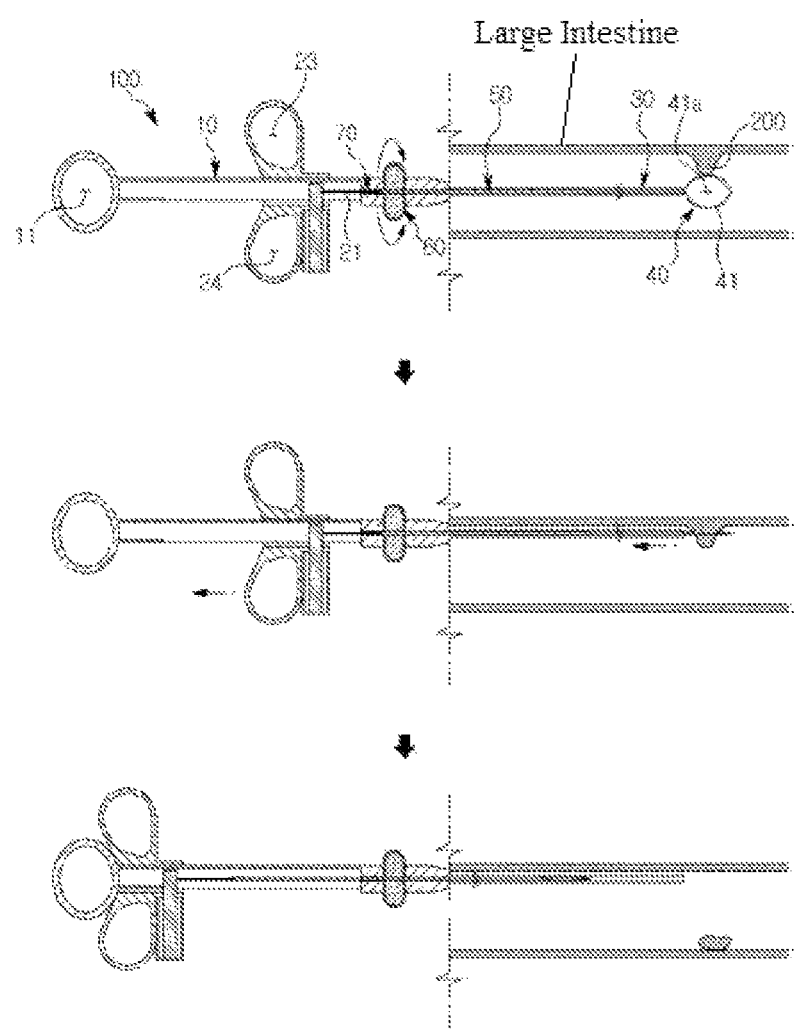
FIG. 7 is an illustrative view showing a surgical procedure of rotating a direction of a loop in order to remove a polyp growing in a large intestine in an arbitrary direction by rotating the wheel of the medical snare according to the present invention.

10: body, 11: first space, 12: exposed space, 13: wheel cover, 14: locking protrusion, 20: movable handle, 21: pusher, 22: catching ball, 23: second space, 24: third space, 30: tube, 40: wire, 41: loop, 50: auxiliary pusher, 51: engaging face, 60: wheel, 61: engaged hole, 62: anti-slide recess, 63: locking recess, 70: connecting pipe, 71: tapered end, 72; connecting end, 100: medical snare

BEST MODE

The present invention is configured so that the expansion direction of a loop is easily rotated in an arbitrary direction in which a removable target has grown, the removable target is easily inserted info the loop so as to allow a surgical procedure to be easily performed to reduce a time required for the surgical procedure and burdens of a patient and a surgeon, and free rotation of a wheel is prevented to be able to fix the expansion direction of the loop.

MODE FOR INVENTION

Hereinafter, exemplary embodiments of the present invention will be described in detail with reference to the accompanying drawings.

As shown in FIGS. 1 to 6, a medical snare of the present invention is configured so that a pusher 21 is coupled in front of a movable handle 20 moving along a cylindrical body 10 in a forward/backward direction, that a wire 40, at a front end of which a loop 41 is formed, is connected to a front end of the pusher 21 along an interior of a tube 30 coupled to the front of the cylindrical body 10, and that tissue is inserted into the loop 41 exposed from the tube 30 by forward movement of the movable handle 20 and is cut by backward movement of the movable handle 20 so as to perform a surgical procedure.

Here, the body 10 has a long cylinder shape and is provided with a first space 11 at a rear end thereof into which a thumb of an operator is inserted. Further, the body 10 is provided with spaces at a front end thereof which are open in opposite directions.

To expatiate on the body, the body 10 is integrally formed with a wheel cover 13 at the front end thereof which surrounds a wheel 60 so that a circumference of the wheel 60 is partly exposed, and one or more locking protrusions 14 protrude from an inner wall of one side of the wheel cover 13.

In the present invention, an example in which two locking protrusions 14 are formed is described. However, three or more locking protrusions 14 may be formed.

In detail, the wheel cover 13 is formed as a track-shaped tube and has exposed spaces 12 formed in the opposite directions. The wheel cover 13 may be formed of a synthetic resin (plastic) material so as to be thin (see FIG. 8).

Moreover, the movable handle 20 is coupled to an outer circumference of the body 10 so as to slide along a length of the body 10 in a forward/backward direction, and is integrally formed with second and third spaces 23 and 24 which are disposed so as to face each other and into which index and middle fingers are inserted.

In this case, an auxiliary pusher 50, on an outer circumference of which engaging faces 51 are formed, is rotatably coupled to a front end of the pusher 21 of the movable handle 20.

These engaging faces 51 of the auxiliary pusher 50 are horizontally parallel with each other, and thus the other faces are formed as a round track.

Here, to rotate the auxiliary pusher 50 relative to the pusher 21, the front end of the pusher 21 is provided with a catching ball 22 whose diameter is larger than that of the pusher 21.

Further, a connecting pipe 70 is configured so that one end thereof functions as a tapered end 71 through which the pusher 21 is to pass and on which the catching ball 22 is caught, and so that the other end thereof functions as a connecting end 72 having a greater diameter than the catching ball 22.

Meanwhile, the auxiliary pusher 50 is fixedly connected to the connecting end 72 of the connecting pipe 70.

When the auxiliary pusher 50 is rotated, the auxiliary pusher 50 and the connecting pipe 70 are configured to be rotated without being separated from the pusher 21.

Further, the wire 40 having the loop 41 is fixedly coupled to a front end of the auxiliary pusher 50.

Furthermore, the wheel 60, in the center of which a engaged hole 61 is formed so as to be fitted around an outer circumference of the auxiliary pusher 50, is installed on the front end of the body 10 so as to not be separated.

In this case, anti-slide recesses 62 are formed along the outer circumference of the wheel 60 so as to prevent fingers from sliding when the wheel 60 is rotated.

In addition, a plurality of locked recesses 63 into which the locking protrusions 14 are inserted and locked are formed in an outer wall of one side of the wheel 60 in a circumferential direction of the wheel 60.

These locked recesses 63 are recessed in a shape in which the locking protrusions 14 can be inserted. In the present invention, eight locked recesses 63 are given as an example.

In the medical snare 100 of the present invention, when the movable handle 20 moves forward/backward, the auxiliary pusher 50 slidably passes through the engaged hole 61 of the wheel 60. Then, when the wheel 60 is rotated, the auxiliary pusher 50 and the wire 40 are rotated so as to be able to switch an open direction of the loop 41 due to engagement of the engaging faces 51 and the engaged hole 61.

An operation and effects of the medical snare configured as described above will be described below.

As shown in FIGS. 1 to 7, a surgical procedure of removing a polyp 200 such as cyst as a spot to be operated on from the large intestine using the medical snare 100 will be described as an example.

To use the medical snare 100 for the surgical procedure, the movable handle 20 is pulled fully backward so that the loop 41 is compressed and inserted into the tube 30.

In this state, the tube 30 is inserted, into the large intestine through the anus along with an endoscope (not shown).

Then, when a position of the polyp 200 is identified through the endoscope, the thumb is inserted into the first space 11 of the body 10, and the index and middle fingers are respectively inserted into the second and third spaces 23 and 24 of the movable handle 20 so as to grasp the medical snare 100 with one hand.

Next, the hand grasping the medical snare 100 is stretched so that the body 10 and the movable handle 20 move away from each other, and thereby the loop 41 is exposed from the tube 30 while being expanded.

Here, when the movable handle 20 moves along the body 10 in a forward direction, the catching ball 22 of the pusher 21 pushes the rear end of the auxiliary pusher 50. Thus, the auxiliary pusher 50 and the wire 40 are pushed forward together, and the loop 41 is exposed from the interior to the exterior of the tube 30.

Further, the engaging faces 51 of the auxiliary pusher 50 slides in the engaged hole 61 of the wheel 60, and the connecting pipe 70 is located at the rear of the wheel 60.

In this way, when the loop 41 is exposed from the tube 30, an operator inserts the polyp 200 into an expanded space 41a of the loop 41. In this state, the operator closes the hand grasping the medical snare 100 so that the body 10 and the movable handle 20 move toward each other.

That is, the loop 41 is pulled into the tube 30 under pressure, and cuts and removes the polyp 200.

When a position at which the polyp 200 has grown is not coincident with the expanded space 41a of the loop 41, the wheel 60 is rotated in a leftward/rightward direction using the other hand with the medical snare 100 grasped with one hand. Thus, the auxiliary pusher 50 and the wire 40 are rotated together since the engaging faces 51 of the auxiliary pusher 50 are engaged in the engaged hole 61 of the wheel 60.

This is because the diameter of the connecting end 72 of the connecting pipe 70 coupled with the auxiliary pusher 50 is greater than that of the catching ball 22 of the pusher 21.

In this way, the expanded space 41a of the loop 41 of the wire 40 is rotated in a direction in which the polyp 200 is easily inserted by the rotation of the wheel 60, so that the polyp 200 growing in any direction can be easily inserted into the expanded space 41a of the loop 41.

Here, when the wheel 60 is rotated to pivot the expanded space 41a of the loop 41, the locking protrusions 14 of the wheel cover 13 are inserted into the locked recesses 63 of the wheel 60. Thus, the loop 41 is not rotated to its original position by a restoring force of the wire 40, and the rotated position of the wheel 60 is fixed. In detail, the wheel cover 13 is formed of a synthetic resin (plastic) material so as to be thin. Thereby, when the wheel 60 is rotated and thus a portion other than the locked recesses 63 passes through the locking protrusions 14 in contact with the locking protrusions 14, the wheel cover 13 is pushed outward. Then, when the locking protrusions 14 are inserted into the locked recesses 63, the wheel cover 13 is restored to its original position by its own elastic force.

Figure 8:
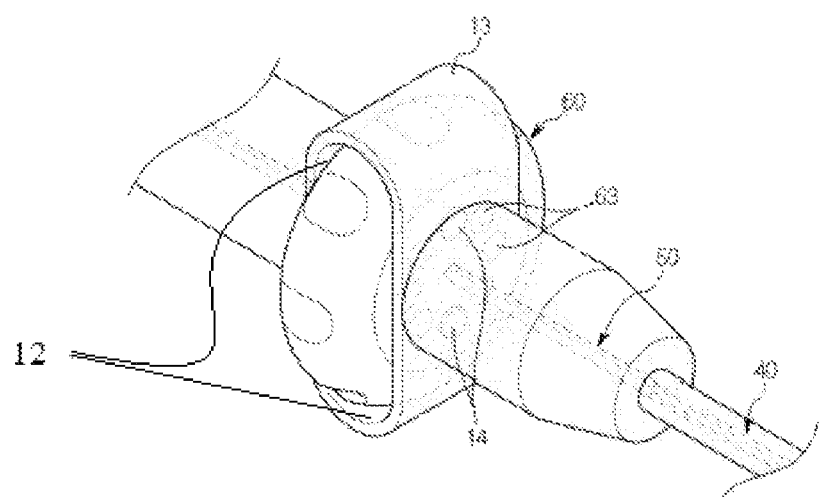
FIG. 8 is a partial perspective view projecting a state in which locking protrusions of a wheel cover according to another embodiment are inserted into locked recesses of the wheel.
Figure 9:
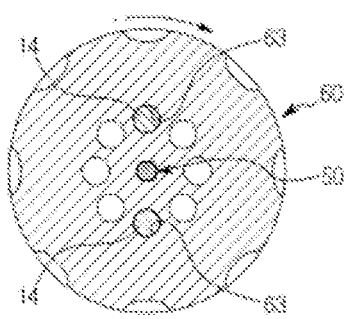
FIG. 9 is an operational view showing a state in which the locking protrusions are locked in the locked recesses when the wheel is rotated.
Figure 9:
Figure 9:
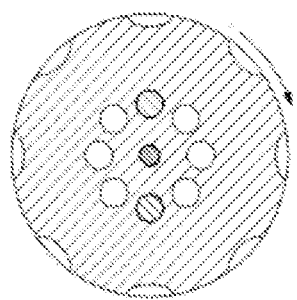
Figure 9:
Figure 9:
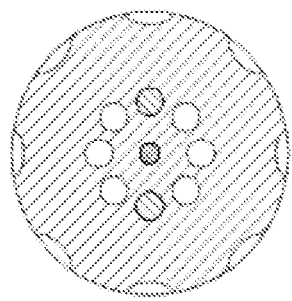
Figure 10:
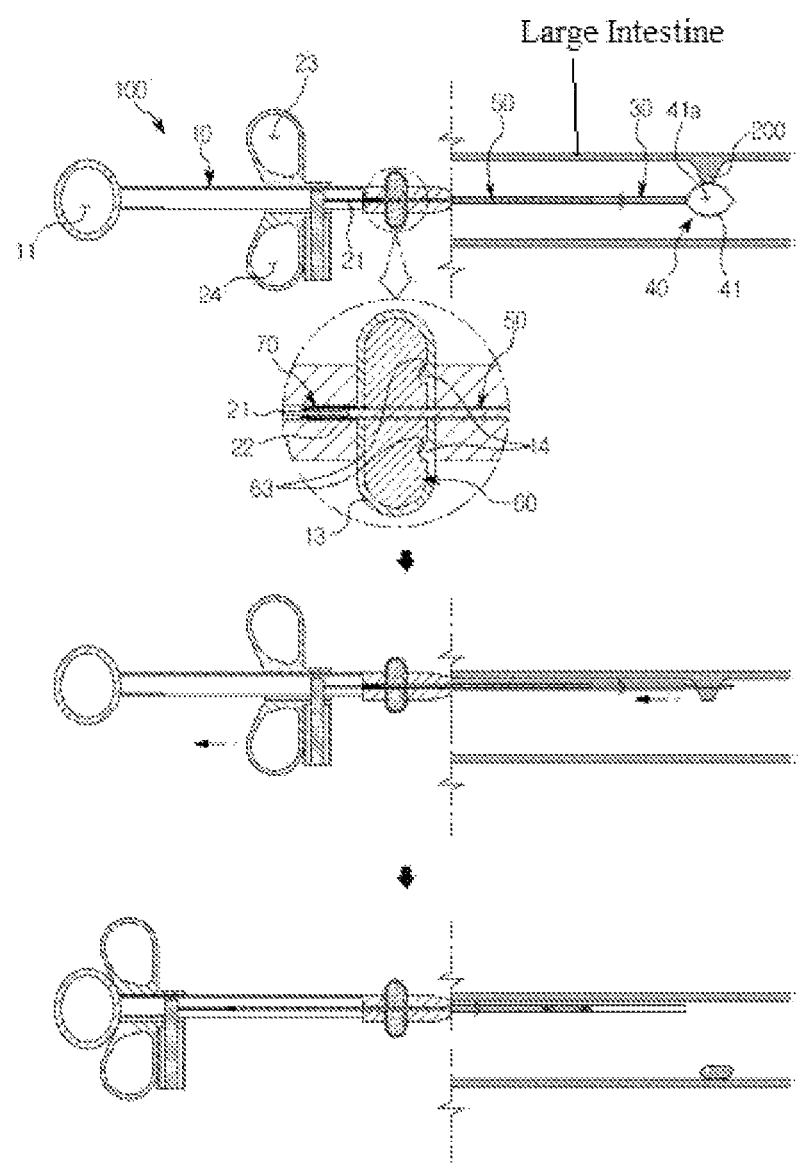
FIG. 10 is an illustrative view showing a surgical procedure of rotating a direction of a loop in order to remove a polyp growing in a large intestine in an arbitrary direction by rotating a wheel of a medical snare according to another embodiment of the present invention.

As a result, the surgical procedure is easily performed with no inconvenience of fixing the wheel 60 so as to prevent the wheel 60 from being rotated to fix the pivoted position of the expanded space 41a of the loop 41 (see FIGS. 8, 9, and 10).

Further, since the engaging faces 51 of the auxiliary pusher 50 are engaged in the engaged hole 61 of the wheel 60, the wheel 60 does not slide when rotated, so that the wheel 60 can be accurately rotated to pivot the expanded space 41a of the loop 41.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A medical snare comprising:
a pusher coupled to a front of a movable handle that moves along a cylindrical body in a forward and backward direction;
an auxiliary pusher having engagement faces on an outer circumference and having a back end rotatably coupled to the front end of the pusher of the movable handle;
a wire having a loop formed at a front end and a back end fixedly connected to a front end of the auxiliary pusher along an interior of a tube coupled to the front of the cylindrical body;
a wheel having an engagement hole in its hub formed to accept the engagement faces of the auxiliary pusher and rotatably installed on the wire at a front side of the body, wherein
when the movable handle moves forward, the auxiliary pusher slidably passes into the engagement hole of the wheel's hub so that the engagement faces engage the engagement hole of the wheel's hub thereby enabling the auxiliary pusher and the wire to rotate so that a direction of the wire loop can align with tissue to be inserted into the wire loop and when the movable handle moves backward, the tissue that was inserted into the wire loop is cut, the auxiliary pusher disengages from the wheel hub thus enabling the wheel to rotate about the wire without changing the direction of the wire loop.

2. The medical snare according to claim 1, wherein the front end of the pusher has a catching ball whose diameter is larger than that of the pusher;
a connecting pipe having a tapered end through which the pusher passes and on which the catching ball is caught, and a connecting end fixedly connected to the auxiliary pusher and having a greater diameter than the catching ball, so that when the auxiliary pusher is rotated, the auxiliary pusher and the connecting pipe are rotated without being separated from the pusher which is not rotated.

3. The medical snare according to claim 1, wherein the wheel includes anti-slide recesses formed along an outer circumference thereof.

4. The medical snare according to claim 1, wherein the body is integrally formed with a wheel cover at the front end thereof which surrounds the wheel so that a circumference of the wheel is partly exposed, wherein the wheel cover includes one or more locking protrusions protruding from an inner wall of one side thereof; and the wheel includes a plurality of locking recesses which are formed in an outer wall of one side thereof in a circumferential direction facing the locking protrusions and into which the locking protrusions are inserted and locked, whereby, when the locking protrusions are inserted and locked into the locked recesses, the wheel cannot rotate to an original position by an elastic force of the wire.

\* \* \* \* \*